United States Patent
Farber et al.

(10) Patent No.: US 11,191,767 B2
(45) Date of Patent: Dec. 7, 2021

(54) PHARMACEUTICAL COMPOSITION FOR STIMULATING STEM CELL DIVISION AND SUPPRESSING BACTERIAL VIRULENCE

(71) Applicants: Boris Slavinovich Farber, Moscow (RU); Sof'ya Borisovna Farber, Moscow (RU)

(72) Inventors: Boris Farber, Brooklyn, NY (US); Sof'ya Farber, Brooklyn, NY (US); Artur Viktorovich Martynov, Kharkov (UA)

( * ) Notice: Subject to any disclaimer, the term of this patent is extended or adjusted under 35 U.S.C. 154(b) by 0 days.

(21) Appl. No.: 16/772,980

(22) PCT Filed: Nov. 15, 2017

(86) PCT No.: PCT/RU2017/000851
§ 371 (c)(1),
(2) Date: Jun. 15, 2020

(87) PCT Pub. No.: WO2019/098869
PCT Pub. Date: May 23, 2019

(65) Prior Publication Data
US 2021/0100801 A1    Apr. 8, 2021

(51) Int. Cl.
| | | |
|---|---|---|
| A61K 31/519 | (2006.01) | |
| A61K 31/04 | (2006.01) | |
| A61K 31/19 | (2006.01) | |
| A61K 31/375 | (2006.01) | |
| A61K 31/4184 | (2006.01) | |
| A61K 31/472 | (2006.01) | |
| A61K 31/4985 | (2006.01) | |
| A61P 31/04 | (2006.01) | |
| A61P 43/00 | (2006.01) | |

(52) U.S. Cl.
CPC ............ *A61K 31/519* (2013.01); *A61K 31/19* (2013.01); *A61K 31/375* (2013.01); *A61K 31/4184* (2013.01); *A61K 31/472* (2013.01); *A61K 31/4985* (2013.01); *A61P 31/04* (2018.01); *A61P 43/00* (2018.01)

(58) Field of Classification Search
CPC .... A61K 31/519; A61K 31/19; A61K 31/375; A61K 31/4184; A61K 31/472; A61K 31/4985; A61P 43/00; A61P 31/04
See application file for complete search history.

(56) References Cited

FOREIGN PATENT DOCUMENTS

| EA | 023447 B1 | 6/2016 |
|---|---|---|
| WO | 2006083779 A2 | 8/2006 |
| WO | 2012112566 A1 | 8/2012 |
| WO | 2013100792 A1 | 7/2013 |

OTHER PUBLICATIONS

Aldenhoff, et al., Studies on a New Strategy for Surface Modification of Polymeric Biomaterials, J. of Biomed. Mats. Res., vol. 29, pp. 917-928 (1995). (Year: 1995).*
Dipiridamol forma vypuska. Oct. 9, 2017 Found on Internet: <http://visexep.mcartur.ru/zaym/dipiridamol-forma-vipuska.php?utm_source= www.google.ru>.
Kazachenko K.JU. Poluchenie i perspektivy primeneniya geneticheski modifitsirovannykh pljuripotentnykh stvolovykh kletok. Klinicheskaya praktika, 2013, No. 2,p. 62, col. 2.
Lin Wenwei et al. Synthesis, Flow Cytometric Evaluation, and Identification of Highly Potent Dipyridamole Analogues as Equilibrative Nucleoside Transporter 1 inhibitors. J. Med. Chem. 2007 50 . 3906-3920 c. 3907 schema 2.
Lee Hong-Kee et al. Combinatorial Mixture Synthesis and Biological Evaluation of Dihydrophenyl Triazine Antifolates. Bioorganic & Medicinal Chemistry, 1999, 7, pp. 1255-1262, the abstract, p. 1257-1258, fig. 1, table 1-3.

\* cited by examiner

*Primary Examiner* — Erich A Leeser
(74) *Attorney, Agent, or Firm* — Daniel M. Cohn; Howard M. Cohn

(57) ABSTRACT

Scope: The invention relates to organic and bioorganic combinatorial chemistry and pharmacia, namely to new combinatorial library of dipiridamol derivative and supramolecular structures based on them, which when being used not separated in individual components, have high bioactivity as a means of stem cell fission encouragement as pharmaceutical compositions combined with phosphodiesterase inhibitors and histone deacetylase inhibitors, as well as pharmaceutically acceptable excipients. The composition can also be used to struggle with resistant microorganisms by establishing their sensitivity to antibiotics.

3 Claims, 2 Drawing Sheets

$R_1;R_2;R_3;R_4=$ H; -CO-CH$_2$-CH$_2$-COOH; -CO-CH$_3$;

PHARMACEUTICAL COMPOSITION FOR STIMULATING STEM CELL DIVISION AND SUPPRESSING BACTERIAL VIRULENCE

FIELD OF INVENTION

The invention relates to organic and bioorganic combinatorial chemistry and pharmacia, namely to new combinatorial library of dipyridamole derivative and supramolecular structure based on them, which when being used, if not separated in individual components, have high bioactivity as a means of stem cell fission encouragement in the form of pharmaceutical compositions combined with phosphodiesterase inhibitors and histone deacetylase inhibitors, as well as pharmaceutically acceptable excipients. The composition is also designed for bacteria virulence depression and recovery of their sensitivity to anti-infective drugs, as well as for production of medical and veterinary biologics, nutrient additives, probiotics and sour-milk ferments on their basis, vaccine production.

PRIOR KNOWLEDGE

Pluripotent stem cells are currently considered to be the most advanced source of youth; they are responsible for angenesis and support physiologically sound immune status. The problem is the decrease of native iPS cells in body with age and correspondingly—ageing. The Japanese scientists (Tanabe et. al., 2013) found the ability of well differential cells to differentiate into pluripotent ones when influenced by genetic vectors. The disadvantage of this avenue is the need for genetic modification of differentiated cells and the hazard of cancer cells formation. The authors managed to find product groups which, in composition, are able to scale up massively the yield percentage stem cells after genetic modification. These are two groups of compounds—cAMP-phosphodiesterase inhibitors and histone deacetylase inhibitors. Though we have not been able to do without genetic modification, the yield of stem cells was increased thousandfold. With this in view, an idea has started up that it is possible to find small-molecule substances able to replace genetic vectors and cause tissue differentiation (reprogramming) into stem ones.

iPS Cells Maturational Stage

Just a small number of cells passes maturational stage successfully shown as low effectiveness of reprogramming in total (Tanabe et. al., 2013). At this stage, epigenetic modifiers allow activating the expression of genes encoding internal pluripotency causes, such as Oct4, Nanog, Sa114, etc. (Feng et. al., 2009).

LIF-STAT signal pathway is essential to iPS cells maturing. For cell culture on a medium free of LIF (leukemia inhibitory factor) serving as an activating ligand of this signal pathway, colonies are formed similar to embryonic stem cells in morphology, but six days later after formation they detach from adhesive surface. Activation of LIF-STAT pathway results in gene promoter demethylation maintaining the pluripotent state. It was demonstrated that transcriptional factor Stat3 blocks directly the DNA and methyltransferase DNMT1 and histone deacylases HDAC2, HDAC3 and HDAC8 (Tang and Tian, 2013).

WNT-signal path way is involved in maturing of iPS cells as adding Wnt3a-activating ligand between the sixth and ninth days after the start of reprogramming increases the number of the formed iPS colonies (Ho et. al., 2013). Such colonies express endogenic Nanog, and maybe the product of this gene is necessary for transition of cells from maturational stage to stabilization stage (Samavarchi-Tehrani et. al., 2010).

iPS Cells Stabilization Stage

Only 1% of cells entering upon reprogramming pathway reach stabilization stage. It is characterized by endogenic expression of pluripotency maintaining factors. It was demonstrated that on the ninth day the phenotypic cell reversion didn't happen in elimination of external factors of reprogramming (Samavarchi-Tehrani et. al., 2010).

At this stage the differences between iPS cells of a mouse and a human can be traced the most clearly. During reprogramming of somatic cells of mice, reactivation of X-chromosome occurs naturally inactivated in females. Reactivation of X-chromosome does not occur in human cells (Plath and Lowry, 2011).

Usage of iPS Cells in Gene Therapy

Possibility of genetic correction of induced pluripotent stem cells provide with a great opportunity to use them in tissue replacement therapy. A large variety of different somatic cell types has been successfully reprogrammed as of today. iPS cells were obtained from neutral stem cells, keratinocytes, B-lymphocytes, peripheral mononuclear blood cells and albuminous (3-cells (Hawkins et. al., 2014).

Experiments for using iPS cells for therapeutic purpose were first made at Jaenisch laboratory. iPS cells, mutation in hemoglobin gene in which was hen eliminated by means of homologous recombination, were obtained from fibroblasts of mices sick with sickle cell anemia. After genetic correction iPS cells differentiated in culture into erythrocyte precursors and were injected into mutant mices where the cells passed final differentiation into erythrocytes in vivo. As a result, absolute recovery of ill animals was observed (Hanna et. al., 2007). iPS cells were also used in replacement therapy of Fanconi's anemia in mices when genetically corrected cells also passed differentiation into erythrocytes in vivo. As a result, recovery of animals was observed (Raya et. al., 2009). Human iPS cells were first obtained from skin fibroblasts (Takahashi et. al., 2007). At the time being, a variety of cells of patients with such diseases as Gaucher disease, muscular dystrophy, Parkinson disease, Huntington chorea, sickle-cell disease has been reprogrammed and researches are carried out in the field of gene-therapy modifications of the obtained iPS cells (Waliaet. al., 2012). iPS cells obtained from patients with different disease can be used to study molecular mechanisms of diseases, search for new drug compounds for therapy, test the effectiveness of already developed drugs and check their toxicity. Such approach was first used to describe the effects from cardioactive compounds on cardiomyocytes differentiated from iPS cells (Yokoo et. al., 2009). iPS obtaining individually from each patient is a long and costly process, often unsuitable for emergency management of such diseases as for example, spinal cord injuries. The best perspective seems to be the creation of bank of iPS cells obtained from the specific selection of donors. The problem of immune response during transplantation of foreign cells can be partially solved by using the donors being homozygotes via histocompatibility HLA gene allele (Takahashi and Yamanaka, 2013). If one of heterozygous donor HLA allel coincide with alleles of homozygote patient, the risk of iPS cells rejection will be minimal. Today the bank of iPS cells obtained from donors with the most popular HLA allels is created in Japan under the supervision of Shinya Yamanaka (Shinya Yamanaka, 2014, verbal communication).

Usage of lentiviral vectors for cells reprogramming.

iPS cells were first obtained by means of simultaneous transduction of four retroviruses carrying Oct4, Sox2, Klf4 and c-Myc (OSKM) (Takashi and Yamanaka, 2006). Retroviruses and Lentiviruses are integrated into host genome ensuring the high level of transgene expression, effective contamination of dividing cells, but along with this there is the risk of insertion mutagenesis and proto-oncogenes activation, thus possibly raising the risk of tumor formation (Okita et al., 2007).

Characteristic of lentiviral vector system.

Lentiviral vector system is based on human immunodeficiency virus-1 (HIV-1), well-studied pathogenic human virus. It possesses a number of properties making it convenient for gene delivery such as broad tropism of targeting cells, ability to contaminate both dividing and non-dividing cells, lack of coat protein expression after transduction, possibility to deliver complex gene elements such as polycistrone or intronic-containing sequences, safety and usability (Sakuma et al., 2012).

While attempting to develop the most safe-for-use vector system, several generations of lentiviral vectors has been developed (Ramezani et al., 2002) among which the third-generation vectors are used the most frequently.

HIV-1 genome is a single-strand RNA molecule with a length of about 9 thousand base pairs, encoding nine coat proteins (Sakuma et al., 2012). Expression products of genes gag, pol and env are respectively the virus core proteins, virus replication ferments and viral surface glycoprotein gp160. Proteins of genes tat and rev activate viral transcription, control the transcript splicing and their export to nucleus. Four remaining genes encode complexing proteins Vif, Vpr, Vpu and Nef. Viral genome contains long terminal repeats (LTR) necessary for reverse transcription and virus integration into genome, as well as packaging signal "ψ".

The first lentiviral vectors were viruses carrying transgenes and capable of replication. For the purpose of safe usage, a series of modifications was carried out as a result of which HIV-1 genome was divided into two plasmids: (i) plasmid containing HIV-1 genome with deletion in gene env; (ii) plasmid expressing Env and not containing packaging signal (Page et al., 1990). Such structure allowed producing viruses able to cause only one round of contamination as gene env necessary to form a complete viral particle didn't enter the cells being contaminated.

Product of gene env, surface glycoprotein gp160 is processed into two proteins, gp120 and gp41. Together they form sub-unit on the surface of viral particle acting as a ligand for molecules CD4, CXCR4 and CCR5. Thus, HIV-1 can contaminate only the cells expressing them: T-lymphocytes, monocytes, macrophages, dendritic cells. In order to increase cell tropism, "pseudotropism" of lentiviral vectors was used by replacing glycoprotein Env for glycoprotein G of vesicular stomatitis virus (VSV-G) (Akkina et al., 1996). VSV-G is able to bind with a widespread cell membrane component phosphatidylserine allowing the vectors to contaminate larger range of cells, including the cells of not the mammals (fish). VSV-G is also much more stable than proteins env thus enabling to obtain larger virus titres in case of ultracentrifugation concentration.

In order to reduce the possibility of accidental formation of lentiviruses able to replicate, the so-called first generation of vectors was created while using transgene delivery lentiviral system. HIV-1 genome was divided into three plasmids: (i) plasmid containing genes gag, pol, as well as genes of regulatory and packing proteins; (ii) plasmid c VSV-G; (iii) plasmid with targeting hybrid proteins. The first two plasmids didn't contain LTR and packing signal which would have enable viral protein genes to get into the viral particles being formed. Thus, only transgene proteins will express in targeting cells. The division into three plasmids also means that at least two recombination events will be necessary to form lentiviruses able to replicate.

Complexing viral proteins Vif, Vpu, Vrp and Nefare required for effective virulence of HIV-1 in vivo. For example, Vif and Vpu neutralize cellular antiviral protective substances APOBEC3G and Tetherin, whereas Nef promotes degradation of molecules MHC I and CD4 (Sakuma et al., 2012). But in case of lentivectors, complexing proteins can be removed without affecting the transfection efficiency.

Thus, the second generation of lentiviral vectors contains just four of nine HIV-1 genes: gag, pol, tat and rev.

Regulatory proteins Tat and Rev are absolutely necessary for HIV-1 replication (Terwilliger et al., 1988). Tat serves as activator and intensifier of viral gene transcription, and Rev promotes nuclear export of viral transcripts to the nucleus. In order to increase safe usage of lentivector system, Rev protein gene is built into the separate plasmid. Also the independence from Tat was achieved by replacing the promoter region in 5'-LTR in plasmid with transgene for strong promoter of cytomegalovirus or respiratory syncytial virus.

The third generation of lentivectors uses four plasmids: (i) plasmid with genes gag and pol; (ii) plasmid expressing Rev; (iii) plasmid expressing VSV-G; (iv) plasmid with transgene. In order to form lentiviruses able to replicate, at least three recombination event would be necessary, but even in this case the obtained viruses would not have had Tat ad complexing proteins.

The reprogramming system was developed at Jaenisch laboratory based on the lentiviruses defective in integrases gene not able to integrate into cells genome. The first lentiviral structure carries the sequence encoding self-cutting polycistronic structure of factors OSKM under the single tetracycline operator promoter. In this structure all four reprogramming factors are divided by self-cutting 2A peptides enabling to synthesize the mixture of relevant transcriptional factors during the translation process. In the presence of doxycycline, transacting protein binds with promoter; its gene sequence is delivered with a help of the second type of lentiviral vector. As a result, simultaneous entering of only two lentiviruses into the cell is necessary for activation of OSKM expression. Heterogeneity of iPS clones obtained with a help of such reprogramming system is far below (Carey et. al., 2009).

The usage of induced pluripotent stem cells is one of the most upcoming trends in treatment of diseases caused by the defects of gene expression. A normal gene replica is inserted into iPS cells obtained from somatic ells of a patient; as a result, its functions recover. DNA delivery to pluripotent cells can be made in a variety of ways, the most promising among them is the usage of artificial chromosomes.

There is a good number of ways to deliver genetic material to the cell. They can be conveniently classified into two groups: those using plasmid vectors or those applying linearized DNA molecules encoding the targeting gene.

The ideal vector for delivery of genetic information shall satisfy a set of the following conditions (acc. to: Kouprina et. al., 2014):

1) possibility to use full-size genes with all endogenous regulator elements;
2) possibility of physiological, native regulation of gene expression;
3) stable long-term expression of entered gene without integration into genome or regulated transient expression;

4) high effectiveness and specificity of targeting cells transfection;
5) lack of risk of cancerous transformation of cells and bringing of immune response.

The most popular viruses used for transmission of genetic material are adenoviruses, adenoassociated viruses, retroviruses (including lentiviruses able to integrate in host genome) and lentiviruses (defective in integrase).

Adenoviruses are the viruses with linear double-strand DNA-genome. It does not integrate into genome of carrier-cell that is why adenovirus cannot contaminate dividing cells effectively. There is also limitation in size of sequence cloned into adenovirus genome (less than 10 Kb) resulting in small amount of capsid. But the main disadvantage in usage of adenoviruses is strong and fast immune response when virus enters the cell.

Adenoassociated viruses are non-enveloped viruses with linear single-strand DNA-genome. They are not autonomous, presence of adenovirus or herpes virus is necessary for replication and expression of viral genome and capsid assembly. In the absence of helper viruses, adenoassociated viruses pass into latent phase and can integrate in the host's cell nucleus only per definite sites of the nineteenth chromosome. Cloning into viral vector is possible only for small sequences (up to 9 Kb). They cause moderate immune response.

Retrovirusis a vector most commonly used for delivery of genetic material. Genome is represented by single-strand RNA molecule. Integration in the host's cell genome occurs promoting the stable expression of transgene. But building-in occurs mostly in sites located near the start spots of transcription on cell genome that can result in insertion mutagenesis (Wu et. al., 2003). Transcriptional transgene silencing can be observed in stem and hematopoietic cells of mouse.

Lentiviruses relate to retroviruses but they can contaminate both dividing and non-dividing cells due to integration into their genome. Lentivector system structure is based on human immunodeficiency virus-1 but it is non-pathogenic and safe to use. Also lentiviruses were created being mutant as per integrase gene and thus not able to build-in into genome. Such viruses provide stable expression of transgene in non-dividing cells and transient—in non-dividing ones (Wanisch and Yanez-Munoz, 2009). Lentiviruses defective in integrase at the moment are one of the most advanced viral system of genetic material delivery.

The main disadvantage of all viral systems of transgene delivery is their small capacity and possibility to use only cDNA of gene without endogenous regulator elements (Kouprina et. al., 2013). Under such conditions, it is impossible to achieve native control of gene expression. Thus, for successful transgene expression in targeting cells, vector is necessary having no limitations in the size of cloned sequence, which is steadily being expressed both in dividing and non-dividing cells, though without integration into genome without causing immune response. The vector system having these properties is artificial chromosomes.

The suggested scheme of synthesis of the combinatorial derivatives based on one polyfunctional parent molecule (for example, dipiridamol) by means of reaction with two and more original modifiers without the following division and separation of each individual derivative is unique and it demonstrated the increase of bioactivity from two to 300 times for different parent molecules: polymyxin, gentamycin, streptomycin, individual oligomeric RNA and DNA, polysaccharoses, proteins, quercetin and many other substances. The important innovation in this approach is correct calculation of molecular ration of reagent quantity: both parent polyfunctional compound (in this case—dipiridamol) and modifiers. In case of correct component ratio, maximum possible combination of derivatives is formed. This mixture is not a classical solution or mixture after the synthesis, and it forms supramolecular structures in aqueuos solutions with each other in random positions and behaves as original dipiridamol, but with more apparent bioactivity and durable action. Formation of supramolecular structures can be traced due to the absence of separation of combinatorial derivative band on chromatographic peak: any changes of separation conditions could not result in separation of mixtures; with that, NMR H1 spectrum demonstrated explicit chaos from hydrogen absorption bands of both methyl groups of residue acetic acid and ethyl groups of residue succinic acid and hydrogens of unsubstituted phenylhydroxyls. The difference from parent molecule is also significant change of bioactivity and its spectrum spreading.

Anti-Microbial Resistance

Lately the observation was made about intensification of developments of the biological ways of microbial biomass production for manufacture of protein drugs, a substantial proportion of which relates to microbially-derived products (vaccines, anatoxins, probiotics, etc.). One of the ways to solve the task for optimization of synthesis of biological protein and non-protein components and build-up of microbial mass is the search and modeling of microbial growth stimulators. A lot of research papers have recently published regarding the study of stimulating effect of different physical, chemical and other factors on biological properties of cells. A wide range bioactivity is characteristics for stimulators with chemical origin—imidazol, isochinoline and their derivatives being a part of the structure of many natural and synthetic compounds able to induce the intensity of microbial population growth. The usage of enhancers is important achievement in the sphere of biotechnological productions, they can increase both percent of biotechnological protein products output and build-up of microbial mass beyond the physiological norm sequence higher. Thus, there is mechanistic potential to significantly increase the speed of microbial mass accumulation and protein products synthesis by microorganisms. Increase of growth and fermentation activity of microorganisms promotes the increase of cell biomass and correspondingly the metabolites for their further effective usage in different industries, in particular in biotechnological, medical and pharmaceutical industry. In order that pathogenic microorganism could cause contagious disease, it shall possess one characteristic—virulence—ability not only to enter the macroorganism and reproduce itself in it but also to depress its defense mechanisms, resulting in the development of contagious disease. Virulence is not a species sign as pathogenicity, but strain one, i.e. it is attributable not to the whole species, but to specific strains. Virulence can also be defined as associated trait of pathogenic genotype of microorganisms. As quantitative character of opposed to qualitative character of pathogenicity, virulence has units of measurement. It can be measured with quantity, i.e. dosage of microorganisms causing specific biological effect. It can be the following:

DCL (dosis certae letalis)—absolute lethal dose—minimum quantity of causative agent causing death of 100% laboratory animals under experiment;

DLM (dosis letalis minima)—minimum lethal dose—minimum quantity of causative agent causing death of 95% laboratory animals under experiment;

LD50—minimum quantity of causative agent causing death of 50% laboratory animals under experiment (most commonly used for virulence measurement).

In addition, the type of laboratory animal used for measurement of this dose shall be always specified as the sensitivity of different types of laboratory animals to this or that microorganisms differs. The microorganism culture injection method shall also be specified mandatorily—abdominal, intramuscular, intranasal, intravenous.

Virulence is a instable sign. It can change both upward and downward, both in vivo and in vitro. In case of maximum decrease of virulence, pathogenic microorganisms can become avirulent, i.e. non-virulent, but virulent microorganisms are always pathogenic. Virulence is implemented through a range of sequential interaction processes between microbial cells and macroorganism cells and tissues:

adhesiveness—ability to attach to the cells;
colonization—ability to multiply on their surface;
invasiveness—ability to enter the cells and surrounding tissues and formation of bioactive products, including the toxins.

Adhesion of microorganisms to macroorganism permissive cell receptors is the most important element of their interaction as if adhesion of microorganisms fails to happen; normally they do not multiply and are removed from the organism. Many microorganisms during evolution gained special morthological and chemical structures which ensure adhesion. They include villi and adhesins—specific structures (proteins and carbohydrates) on the surface of microbial cell corresponding to the macroorganism cell receptors.

TERMINOLOGY

Acylation—injection of residue acylRCO-(acyl) to the organic compound, normally by substituting the hydrogen atom, injection of residue acetic acid $CH_3CO$ is called acetylation, benzoic acid $C_6H_5CO$— benzoylation, formic acid HCO— formulation. Depending on the atom to which the residue acyl is attached there can be C-acylation, N-acylation, O-acylation. Halogen anhydrids and acid anhydrides are used as acylating agents.

Alkylation—injection of alkyl substituent into molecule of organic compound. Typical alkyl agents are alkyl halides, alkenes, epoxy compounds, alcohols, more rarely aldehydes, ketones, ethers, sulfides, diazoalkane. Alkylation catalysts are mineral acids, Lewis acids as well as zeolites. Alkylation is widely used in chemical and petroleum industries.

Combinatorial synthesis—synthesis by means of combinatorial chemistry methods; it includes simultaneous reaction between three and more reagents with formation of combinatory synthesis product consisting of dozens of derivatives. Then these derivatives are separated by chromatography, their structure is confirmed and their bioactivity is studied.

Simultaneous combinatorial modification with two modifiers—if combinatorial synthesis reaction uses polyfunctional molecule with more than two groups available for modification and two modifying agents are introduced simultaneously into reaction, for example, acetic anhydride and succinic anhydride. As a result of reaction, mixture of acylated derivatives is formed in different positions—acetyl-succinyl derivatives.

Combinatorial library [Lat. combinare—combine, join; Greek. biblion—book and theke—storage]—set of many all kinds of chemical compounds, proteins, genes or oligonucleotides enabling to carry out fast search of targeted genes or targeting proteins. For example, a set consisting of millions of different chemical substances, or a complex of recombinant DNA molecules obtained by building-in into cDNA vector of light and heavy chains of different antibodies, etc.

Stem cells—undifferentiated pluripotent (immature) cells which many species of multi-cellular organisms have. Stem cells can self-renew forming new stem cells, divide by means of mitosis and differentiate in specialized cells, i.e. pass into cells of different organs and tissues. Development of multi-cellular organisms starts with one stem cell generally known as zygote. As a result of numerous division cycles and differentiation process, all kinds of cells are formed peculiar for this biological species. There are about 220 such types of cells in human body. Stem cells continue to exist and function also in adult body; thanks to them renewal and recovery of tissues and organs is possible. However, their quantity reduces in the process of body ageing. Modern medicine deals with transplantation of human stem cells, i.e. they can be grafted medicinally. For example, transplantation of hematopoietic stem cells is carried out for hemapoiesis process recovery (blood-forming) when treating leucosis and lymphomas.

Regeneration (recovery)—ability of living organisms to recover lesional tissues over time, and sometimes even the whole lost organs. Regeneration is also called the recovery of the entire organism from its artificially separated fragment (for example, recovery of freshwater hydroids from a small fragment of body or dissociated cells). Regeneration of protistansis demonstrated as recovery of lost cell organs or cell parts. Regeneration occurring in case of damage or loss of any organ or body part is called reparative. Regeneration in the process of normal activity of organism usually not connected with damage or loss of a part of the body is called physiological. Human epidermis regenerates well; its derivatives like nails and hair are able to regenerate too. Bone tissue is able to regenerate as well (bones get fused together after fractures). After loss of liver (up to 75%), the remaining fragments start grow in size due to enlargement of the cells but not due to increase of their quantity. Thus, liver recovers its initial mass completely. Under specific conditions, finger tips can regenerate. Until recent times it was generally believed that nervous system is not able to regenerate, but the latest discoveries demonstrated that CNS features neurogenesis, i.e. ability to create new neurons and afterwards to form new synaptic compounds.

Regeneration is called reparative when it takes place after damage or loss of any part of the body. There are typical and atypical reparative regeneration. In case of typical regeneration, lost part is substituted by means of development of the same part. The cause for loss can be external action (for example, amputation) or an animal takes off a part of its body deliberately (autotomy), like a lizard breaking off a part of its tail in order to escape from the enemy.

In case of atypical regeneration, the lost part is substituted by structure different from the initial one in terms of quality or quantity. Number of fingers in regenerated limb of frog larva can be less than in initial one; and in case of a shrimp, antennae can grow instead of amputated eye (heteromorphosis).

Phosphodiesterase (PDE)—a group of ferments hydrolyzing the phosphodiester bond (sub-subclass EC 3.1.4). Generally they include DNAases, RNAases, cAMP-phosphodiesterases, cGMP-phosphodiesterases, phospholipase C and phospholipase D. Sometimes this term means narrower group of ferments involved in regulation of signal pathways, i.e. foremost cAMP-phosphodiesterases and cGMP-phosphodiesterases.

Phosphodiesterase inhibitors. Pharmacological action of Sildenafil and its analogues is caused by specific competitive inhibition of cAMP-PDE type 5 of cavernous body resulting in rise of cAMP level in tissue and further vasodilatation due to increase of NO release. Inhibitors of PDE 4 type are important for the therapy of chronic obstructive pulmonary disease as anti-inflammatory agents modifying the disease state. Such drugs include roflumilast and cilomilast. Domestic doctors know roflumilast as Daksas. Other inhibitors of PDE 4: Ampremilast. Inhibitors of PDE 3: Cilostazol.

Histone deacetylases (HDACs), (EC 3.5.1)—ferments catalyzing the removal of acetyl group ε-N-acetyl-lysinhistones introduced by ferments histone acetylases (HATs) to residual K3 and K14 histone H3 and K5, K8, K12 and K16 histone H4, as well as some residually lysines of histones H2A and H2B. By modifying histones and changing chromatin conformation, histone deacetylases are essential for regulation of gene expression. Whereas the hyperacetylation of histones under action of histone acetylasesis normally connected with increase of transcriptional activity, histone deacetylases cause hypoacetylation and as a result gene repression. Hypoacetylation results in reduction of space between nucleosome and DNA wounded around it. Denser DNA packing reduces its availability for transcriptional factors resulting in transcriptional repression. Histone deacetylases usually act as a part of large complexes together with other proteins depressing chromatin activity. The substrates of histone deacetylases can be not only histones but also some other proteins (p53, E2F, a-tubulin and MyoD). The family consists of 18 proteins belonging to 4 classes. 11 representatives belonging to I (reduced potassium dependency 3 (RPD3)-like; HDAC1, HDAC2, HDAC3, HDAC8), II (class yeast histone deacetylase 1, Hdal; not to be confused with HDACI!; HDAC4, HDAC5, HDAC6, HDAC7, HDAC9, HDAC10) and IV classes (HDAC11) are called "classical" histone deacetylases, whereas the representatives of class III are called sirtuins. The representatives of class I and II are inhibited with trichostanin A (TCA, TSA), whereas the representatives of other classes are insensitive to it.

Histone deacetylase inhibitors (HDACi). At the present moment there is a range of histone deacetylase inhibitors starting from complex compounds taken from bacteria and fungi (TCA, tapoxyne) and ending with relatively simple compounds (butyrate). Most HDACi have triple-component structure consisting of zinc-relating area, linker and sequence interacting with amino-acid residues at the inlet to active center of HDAC. Inhibitors of classical deacetylases function by means of displacement of zinc ion from active center and thus inactivating the charge change system. TCA possesses optimal conformation for entering the active center having hydroxamate group and five-carbon linker before phenyl group. TCA causes the strongest reversible effect among all known HDACi (its IC50% is located in nanomolar region). HDACi cause hyperacetylation, transcription activation, and, according to some sources, active DNA demethylation. As HDACi slow down the growth and cause differentiation and apoptosis of cancerous cells, active developments are carried out aimed at their usage for cancer treatment (Vorinostat, Romidepsin, Belinostat). HDACi induce apoptosis, cell cycle arrest, ageing, differentiation, cell immunogenicity and inhibit angiogenesis in case of some types of cancer. The best examples of HDACi usage are Vorinostat and Romidepsinin patients with refractory cutaneous and peripheric T-cellular lymphoma. In accordance with chemical structure, there are 4 classes of HDACi—hydroxamates, cyclic peptides, aliphatic acids and benzamides. Most part of information about these molecules is based on cancer researches. Hydroxamates mainly belong to pan-HDACi (non-specific HDACi). Hydroxamates are represented with trichostachine A (TSA) which inhibits the growth of cells in case of lung and breast cancer and is pan-cellular inhibitor of HDAC. TSA didn't become clinical practice due to adverse experience—apoptosis of normal cells and DNA damage. Suberanilohydroxamic acid (SAHA) (Vorinostat) is also hydroxamate, this is the first HDACi approved by FDA for clinical use. Its effect causes activation of antiproliferative genes p21WAF1, p27 KIP1, DR5 and TNFα, and reduction of activity of positive growth regulators: CDK2, CDK4, cyclin D1 and cyclin D2. Today a variety of molecules from hydroxamate class are studied: e CBHA, LAQ-824, PXD-101, LBH-589, ITF2357, oxamflatin, ABHA, SBHA, Scriptaid, pyroxamide, SK-7041, SK-7068 and tubacine. Recently the activity of pan-HDACi regarding HDAC of class IIa is called into question but as a result of more detailed researches "true" pan-HDACi are detected, for example pandakostat. Future trends of pan-HDACi are complexified with the fact that they are ineffective regarding the solid tumors, but its reasons remain unknown. Today substantial attention is paid to the development of HDACi selective to definite isoforms of HDAC. However, searches of new pan-HDACi continue. The testimony of it is actions of pharma companies: thus, in September, 2014 Servier and Pharmacyclists companies conclude agreement on joint development of abexinostat and other compounds. "New generation" an-HDACi appear such as givinostat, continue and clinical tests of "old" HDACi such as panabinostat as a part of mono- and combination therapy, including solid tumors.

Composition (US Patent Application US20080103165A1 Ppar mediated modulation of neurogenesis) is known which is a set of methods of treating diseases and conditions of central and peripheral nervous system, including by stimulation or increase of neurogenesis, neuroproliferation and/or neurodifferentiation. It includes compositions and methods based on the usage of agents activating peroxisoma receptors (PPAR), not necessary combined with one or several other neurogenic agents, for stimulation or increase of neurogenic response and/or for disease treatment. Pharmaceutical composition includes modulators of phosphodiesterase, histone deacetylase, modulators of GABA-receptors and other substances. Disadvantage of invention is field-specific purpose of composition—stimulation of neurogenesis only through stimulation of division of stem cells—neuron precursors; besides, the authors didn't demonstrate the influence of the mentioned substances on pluripotent stem cells and on immunity. The composition does not also have combinatorial dipirimadol derivative with two modifiers, enabling to substitute simultaneously all known phosphodiesterase inhibitors and manifests as combination of ability to stimulate division of stem cells combined with histone deacetylase inhibitors. There is a known method of depressing the bacteria virulence by adding the effective quantities of phenylpropanoid inhibitors to culture medium [US Patent Application Publication U52010/0249234 A1 Sep. 30, 2010 (Methods of reducing virulence in bacteria) Ching-Hong Yang]. Disadvantage of this invention is obvious genotoxicity of the added component and impossibility to use it in medicine. Although the substance depressed the expressed virulence factors, it affected only the genes, moreover irreversibly. Though such bacteria lost virulence factors, they became distinct mutants and heritage low virulence signs in future generations. Our composition causes no mutations, it does not have genotoxicity. The disadvantages specified for the given analogues can be eliminated by using pharmaceutical composition based on histone deacetylase inhibitors and cAMP-phosphodiesterase inhibitors ("combinatorial dipirimadol derivative with two modifiers substituting simultaneously all known phosphodiesterase inhibitors".) combined with combinatorial mixture of binary modified dipirimadol derivatives. This combination demonstrates several super-effects: except for the stimulation of pluripotent cells division, it can activate regeneration of tissues in case of wounds, unwrinkled via tissue rejuvenescence, modulate immune system. Also in the presence of this composition, resistance bacteria lose many virulence factors, become sensitive to classical antibiotics.

INVENTION DISCLOSURE

Aim of invention is to create pharmaceutical composition designed for activation of tissue regeneration, stimulation of stem cells division, as well as able to depress virulence of microorganisms; in future this will allow using this composition for treatment of contagious diseases in humans and animals by applying enhancers before the course of antimicrobial therapy.

The determined aim can be achieved by creating the pharmaceutical composition including phosphodiesterase inhibitors, incl. dipirimadol, and histone deacetylase inhibitors, as well as pharmaceutically acceptable excipients, which also contains unseparated mixture of dipiridamol combinatorial derivatives obtained by means of simultaneous modification by at least two covalent modifying agents. Also the following combinations can be used as covalent dipiridamol modifiers: succinic anhydride and monochloroacetic acid; maleic anhydride and succinic anhydride; maleic anhydride and monochloroacetic acid or any other two modifiers from the list: acetic anhydride, propionic anhydride, butane anhydride, acetic-propionic anhydride, acetic-butane anhydride, glutaricanhidride, phthalic anhydride, cis-aconiticanhydride, trans-aconitic anhydride, citric anhydride, isocitric anhydride, acetyl chloride, acetyl fluoride, propionyl chloride, butyroilchloride, ethoxyoxalylmonochloride. The pharmaceutical composition can also additionally contain ascorbic acid as anti-oxidant and bendazol as adenylate cyclase inhibitor.

PHARMACEUTICAL COMPOSITIONS

Figure 1:
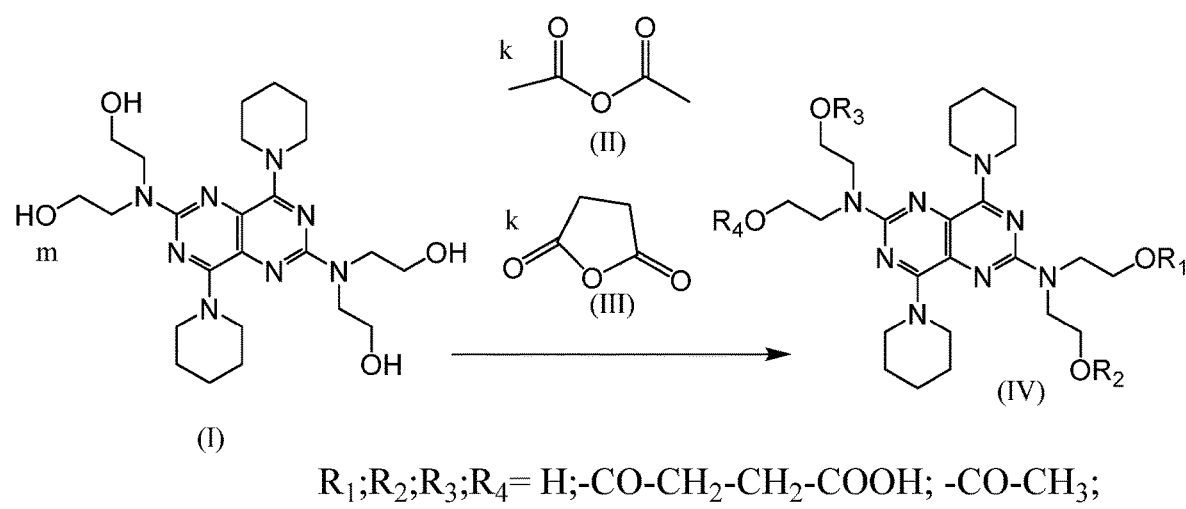
FIG. 1. Scheme of combinatorial dipiridamol derivative synthesis (IV) in combinatorial reaction of dipiridamol (I) with two modifiers (II, III).

Different methods can be used to introduce the supramolecular combinatorial dipiridamol derivative (SCDD). SCDD composition can be administered orally or as intravascular, subcutaneous, intraperitoneal injection, in aerosol form, via eye, in bladder, locally, etc. For example, inhaled administration methods are well known in this technical field. Dose of pharmaceutical composition will vary over a wide range depending on the specific administered SCDD, nature of disease, frequency of administration, administration method, clearance of the used agent from host organism and the like. Initial dose can be higher with the following lower maintaining doses. The dose can be administered with a frequency of one time per week or every other week, or can be divided on smaller doses and administered once or several times a day, twice a week and so on for maintaining the dose efficacy level. In many cases, higher dose will be required for oral administration than for intravascular administration. Within this invention, SCDD can be included to many compositions for therapeutic administration. In detail, within this invention SCDD can be included to pharmaceutical compositions combined with suitable pharmaceutically acceptable carriers or diluents and can be included to preparations with solid, semisolid, liquid or gaseous forms such as capsules, powders, granules, balms, creams, foams, solutions, suppositories, injections, forms for inhalation, gels, microspheres, lotions and aerosols. SCDD, as it is, can be administered in different ways, including oral, buccal, rectal, parenteral, intraperitoneal, subcutaneous, percutaneous, intratracheal administration and so on. According to invention, SCDD, after being administered, can be distributed on the system level or can be localized using implant or another composition holding down the active dose in the place of implantation. According to this invention, SCDD can be administered independently, combined with each other or they can be used combined with other known compounds (for example, ascorbic acid, bendazol, anti-inflammatory agents, etc.). SCDD can be administered to pharmaceutical dosage forms as their pharmaceutically acceptable salts. The following methods and excipients are mentioned only as examples and are not restricting by any means. For preparations with oral administration method, compounds can be used independently or combined with suitable additives for manufacture of pills, powders, granules or capsules, for example, with ordinary additives such as lactose, mannitol, corn starch or potato starch; with linking agents such as crystalline cellulose, cellulose derivatives, gum acacia, corn starch or gelatines; with disintegrators such as corn starch, potato starch orsodium carboxymethyl cellulose; with lubricating agents such as talc or magnesium stearate; and, if desired, with dilutants, buffering agents, wetting agents, preserving agents and correctives. SCDD can be included to compositions for injections via their dilution, suspending or emulsionizing inaqueous or nonaqueous solvent, such as vegetable or other similar oils, synthetical glycerides of aliphatic acids, ethers of higher aliphatic acids or propylene glycol; and, if desired, with ordinary additives such as solubilizers, isotonic agents, suspending agents, emulsifiers, stabilizers and preservatives. SCDD can be used in aerosol composition for inhaled administration. According to this invention, SCDD can be included to acceptable propellants under pressure such as dichlorodifluoromethane, propane, nitrogen, etc. Besides, compounds can be included in suppositories by mixing with a variety of bases such as emulsifying bases or water-soluble bases. According to this invention, SCDD can be administered rectally using suppository. Suppository can contain fillers such as cacao shell butter, carbowaxes and polyethyleneglycols melting at body temperature, though solid ones—at room temperature. Standard dosage forms can be manufactured for oral or rectal administration such as syrups, elixirs and suspensions, where each dose unit, for example, teaspoon, tablespoon, pill or suppository, contains predefined quantity of composition containing one or more compounds within this invention. Similarly, standard dosage forms for injections or intravascular administration can contain SCDD as per this invention in composition in the form of sterile water solution, normal physiological salt solution or other pharmaceutically acceptable carrier.

Implants for long-term release of compositions are well known in this technical field. Implants are produced in the form of microspheres, bars, etc. with biodegradable or non-biodegradable polymers. For example, lactic and/or glycolic acid polymers form degradable polymer well tolerated by host. Implant containing SCDD as per invention shall be placed close to trauma focus so that local concentration of active agent is higher compared to remaining body regions. The term "standard dosage form" used here refers to physically discrete units suitable for usage as single doses for human and animal subjects; by this, each unit contains predefined quantity of compounds as per this invention sufficient, according to calculations, for desired effect, together with pharmaceutically acceptable diluent, carrier and filler. Descriptions of standard dosage forms as per this invention depend on the specific SCDD being used, as well as on the effect to be achieved, and on the pharmacodynamics of used compound in the host. Pharmaceutically acceptable excipients such as fillers, adjuvants, carriers or diluents, are generally accessible. Besides, pharmaceutically acceptable auxiliary substances are generally accessible, such as pH controlling agents and buffering agents, tonicity controlling agents, stabilizers, wetting agents, etc. Typical doses for system administration vary from 0.1 pg to 100 milligram per kg subject body mass for one administration. Typical dose can be one pill for administration from two to six times a day or one capsule or pill with long-term release for intake once a day with proportionally higher content of active ingredient. Long-term release effect can be caused by materials a capsule is made from, dissolving at different pH values, capsules providing slow release affected by osmotic pressure or any other method of controlled release. It will be clear to the specialists in this technical field that dose levels can vary depending on the specific compound, severity of symptoms and subject's liability to side effects. Preferred SCDD doses can be easily determined by specialists in this technical field by a variety of ways. The preferred method is measurement of SCDD bioactivity. One of the methods of interest is usage of liposomes as a filler for delivery. Liposomes merge with cells of target area and provide delivery on liposome content inside the cells. Contact of liposomes with cells shall be maintained for a time sufficient for merging, using different methods to maintain the contact such as extraction, linking agents and the like. In one aspect of invention, liposomes are developed to obtain aerosol for pulmonary administration. Liposomes can be made with purified proteins or peptides mediating the merging of membranes such as Sendai virus or influenza virus, etc. Lipids can represent any useful combination of known lipids forming liposomes, including cationic or zwiterionic lipids such as phosphatidylcholine. The remaining lipids will be normally neutral or acidic lipids such as cholesterin, phosphatidylserine, phosphatidylglycerol and the like. In order to obtain liposomes, we can use method described by Kato et al. (1991) J. Biol. Chem. 266:3361. In short, lipids are mixed with SCDD-containing composition for presenting to liposomes in the suitable water medium, in salt medium properly, where total solids will be within a range of 110 wt. %. After vigorous mixing within short periods of time, about 5-60 sec., glass tube is placed in warm water bath at about 25-40° C. and this cycle is repeated about 5-10 times. Then the composition is processed with ultrasound within suitable period of time, normally about 1-10 sec., and, possibly, is additionally mixed with vortex mixer. Then the volume is increased by adding water medium, normally about 1-2 times, with further shaking and cooling. This method allows including supramolecular structures with high cumulative molecular weight to liposomes.

Compositions with Other Active Agents

According to formula, the composition may include such phosphodiesterase inhibitors as vinpocetine, nicardipine, nimodipine, lixazinone, cyclostamide, milrinone, cilostazol, dihydropyridazinone, rolipram, denbufillin, cilomilast, roflumilast, sildenafil, ariflo, vardenafil, tadalafil, zaprinast, thiadiazole, papaverine, but the composition is not limited by the specified substances. The composition may also include histone deacetylase inhibitors: valproic acid, valproic-hydroxamic acid, cinnamichydroxamic acid, phenyl butyrate, tubacin, vorinostat, depsipeptide, butyrate, but the composition is not limited by the specified substances. For application in methods under consideration, according to invention SCDD may be included into compositions with other pharmaceutically active agents, in particular antimicrobial agents, immunomodulators, antiviral agents, and antiviral substances. Other agents of interest include a wide range of antibiotics known in this technical field. Antibiotic classes include penicillins, for example penicillin G, penicillin V, methicillin, oxacillin, carbenicillin, nafcillin, ampicillin and so on; penicillins in combination with betalactamase inhibitors; cephalosporins, For example cefaclor, cefazolin, cefuroxime, moxalactam, etc.; carbapenems; monobactams; aminoglycosides; tetracyclines; macrolides; lincomycins; polymyxins; sulfonamides; quinolones; chloramphenicol; metronidazole; spectinomycin; trimethoprim; vancomycin; and so on. Antifungal agents are also useful, including polyenes, for example amphotericin B, nystatin, flucosin; and azoles, for example miconazole, ketoconazole, itraconazole and fluconazol. Tuberculosis drugs include isoniazid, ethambutol, streptomycin and rifampin. Other agents of interest in terms of creating new compositions include a wide range of mononucleotide derivatives and other RNA polymerase inhibitors known in this technical field. Classes of viral inactivating agents include interferons, lamivudine, ribavirin and so on; amantadine; remantadine, For example zinamivir, oseltavimir and so on; acyclovir, valacyclovir, valganciclovir; and so on. Other groups of viral inactivating agents include adefovir, vbacavir, didanosine, emtricitabine, lamivudine, stavudine, tenofovir, efavirenz, nevirapine, indinavir, lopinavir and ritonavir, nelfinavir, ritonavir, sakinavir, daclatasvir, sovofbuvir. According to invention SCDD composition may also cytokines, for example interferon gamma, tumor necrosis factor alpha, interleukin 12, etc. The present invention is further described by the following examples which should not be considered as limiting the scope of the invention.

Example 1. Obtainment of Supramolecular Combinatorial Dipiridamol Mixture (CD)

Dilute 222 μM of dipirimadol (I) (CAS N 58-32-2, Mr=504.636 g/mol, n=4) in 50 ml of dioxane in mixture with 50 ml of glacial acetic acid, add 60 μM of succinic anhydride (III) and 61 μM of acetic anhydride (II), stir the solution and warm with backflow condenser within 5-50 minutes. Pour the solution into vials and lyophilize to remove solvent and acetic acid. Combinatorial mixture (IV) is used to obtain pharmaceutical compositions, to study structures, to determine bioactivity (CD). FIG. 4 shows the scheme of combinatorial dipiridamol derivatives synthesis. Instead of carboxylic acid anhydride modifiers, you can use halides of carboxylic and polycarboxylic acids, such as succinic, maleic, fumaric, lactic, propionic, other halogen derivatives, such as chloromethane, bromoethane, chloropropane, cyclic alkylating compounds like oxirane, propiolactone.

FIG. 1.

One parent molecule of diprimadol (I) contains 4 residual hydroxyl groups available for modification (n=4). The amino groups as a part of residual morpholine and the pyridmidine nucleus—protonated and protected against modification under the given reaction conditions.

Calculations of the number of modifier moles are carried out according to the combinatorics formulas:

$$m=4\times(3\times2^{n-2}-1);$$

$$k=n\times(2^n-1),$$

where m—number of different molecule derivatives in the combinatorial mixture and the number of dipyridamole moles for reaction; n—number of hydroxyl groups available for modification in the structure of dipyridamole (n=4); k—number of moles of each modifier. Thus, having only one parent dipyridamole molecule and two modifiers after combinatorial synthesis, we obtain 12 combinatorial derivatives with different degrees of substitution, different positions of the substituents and different shufflings of the modifier residues, not just as a mixture, but as difficultly separated supramolecular mixture. Due to the presence of both substituted and non-substituted hydroxyl groups in different derivatives, supramolecular structures are formed through both hydrogen and ionic bonds, including with tertiary amino groups of heterocycles. Modifiers—succinic anhydride or acetic anhydride can be introduced both simultaneously and sequentially—or first introduce succinic anhydride, warm the mixture with backflow condenser, and then introduce acetic anhydride and reheat the mixture. Similarly, in this reaction, maleic anhydride, aconitic anhydride, glutaric, phthalic anhydride and acetic anhydride, ethyl formic acid, monochloroacetic acid, propiolactone, ethylene oxide and other low-molecular alkylating agents (methyl chloride, ethyl chloride, propyl chloride) can be used instead of succinic anhydride as one of the modifiers.

NMR $C^{13}$ (carbon-13-nuclear magnetic resonance): C: 96,1; 161,8; 170,0; 157,8; $CH_2$: 58,9; 61,7; 58,1; 61,4; 29,2; 29,1; CO: 173,1; 174,7; 170,2; $CH_2$ (in morpholine cycle) 52,7; 25,4; 25,5$C^{13}$ NMR data of the combinatorial derivative confirm the presence of both ethyl groups of succinic acid residues in its structure and acetyl residues—reaction products with acetic anhydride.

For HPLC we used Milichrom A-02 microcolumn chromatograph in the gradient of acetonitrile (5-100%)/0.1 M chloric acid+0.5 Mlithium perchlorate. The combinatorial derivative in the chromatogram gave one clear broadened peak and was not separated into components, although the retention time differed from both the starting dipyridamole and its completely substituted derivatives. This indicated that complex supramolecular structures that were not separated chromatographically formed between different combinatorial derivatives (in our case, there were 12 of them). This combinatorial derivative (CD) also behaves similarly when separated in a thin layer (acetonitrile: water, UV detection) and gives only one band that does not coincide with any of the obtained derivatives.

FIG. 2.

Figure 2:
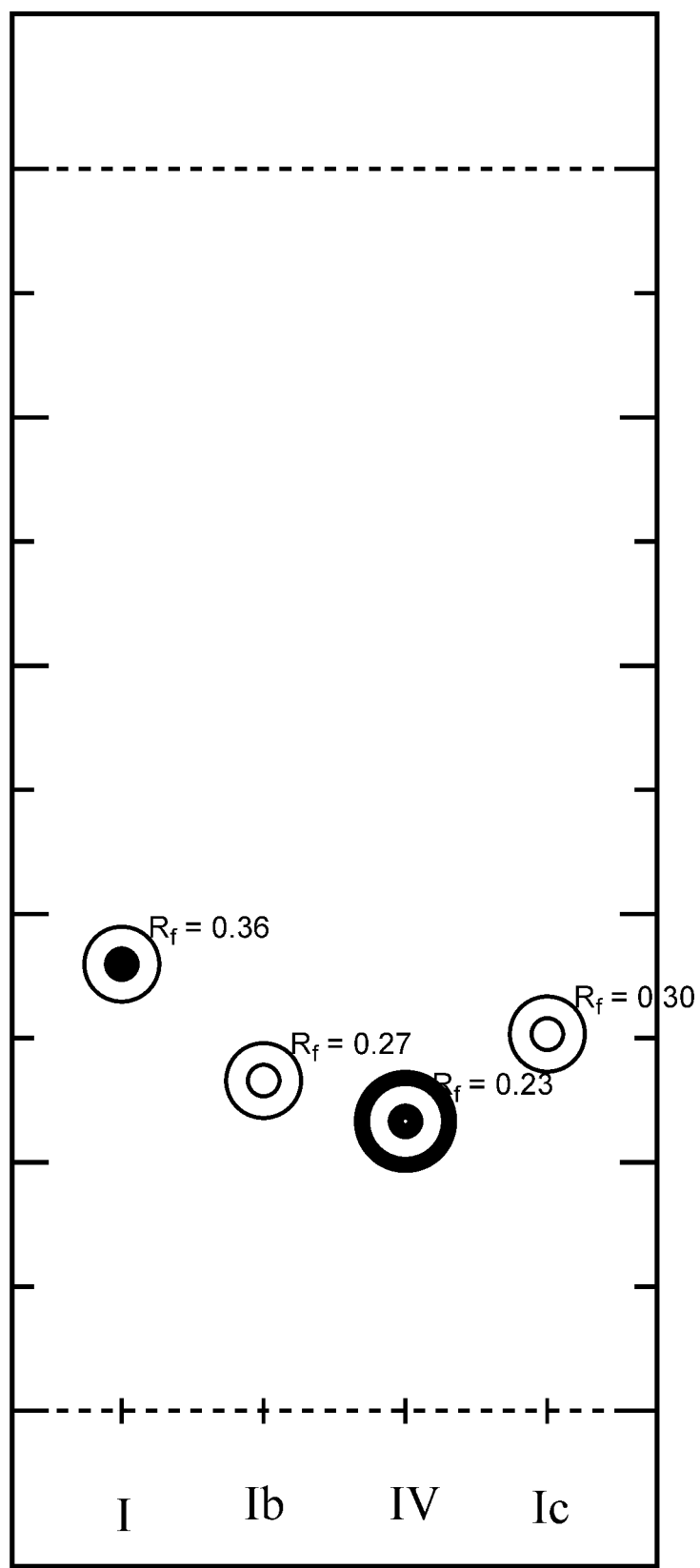
FIG. 2. Thin-layer chromatogram of combinatorial dipiridamol derivative (IV), initial dipiridamol (I), completely acylated dipiridamol (Ib) and completely succinylated dipiridamol (Ic).

As FIG. 2 shows, TLC, combinatorial mixture (IV) is less mobile, while the initial unmodified dipyridamol (I) is the lightest. Completely acylated dipyridamol (Ib) and succinylated dipyridamol (Ic) are intermediate between native dipyridamole and combinatorial one. The combinatorial dipyridamole band is not separated either by two-dimensional TLC or by HPLC (not shown).

Next, a study was conducted of the inhibition of cAMP-phosphodiesterase from supramolecular combinatorial dipyridamole derivatives obtained in the reaction with different molar ratios of modifiers according to the final concentration of AMP by ELISA method. The reaction was stopped by the addition of a double volume of 1% TCA.

TABLE 1

Inhibiting property regarding cAMP-phosphodiesterase (PDE) from supramolecular combinatorial derivatives of dipiridamol obtained in the reaction with different molar ratio of modifiers

| Item No. | Reagent molecular ratio* | | | $ED_{50}$ as related to cAMP, µg/ml, measuring error 10% |
|---|---|---|---|---|
| | m | k1 | k2 | |
| 1 | 44 | 88*** | 88*** | >500 |
| 2 | -//- | 70 | 70 | 100 |
| 3 | -//- | 61 | 60 | 0.01 |
| 4 | -//- | 30 | 30 | 5 |
| 5 | -//- | 15 | 15 | 10 |
| 6 | -//- | 7 | 7 | 60 |
| 7 | -//- | 3 | 3 | 115 |
| 8 | -//- | 2 | 2 | 210 |
| 9 | -//- | 1 | 1 | 300 |
| 10 | -//- | 0 | 0 | 300 |

*m-number of moles of dipyridamol in the combinatorial synthesis reaction; k1-number of moles of succinic anhydride in the reaction; k2-number of moles of acetic anhydride in the reaction;
** $ED_{50}$ µg/ml of PDE inhibition was determined by diluting the initial concentration of the dipiridamol derivative;
***maximum molar ratio at which all groups in dipiridamol are replaced, exceeding this ratio leads to the fact that in the reaction unreacted modifiers-succinic anhydride and acetic anhydride remain in medium.

As Table 1 shows, the smallest $ED_{50}$ is observed precisely in the region with calculated molar ratios of modifiers (44:61:60). Thus, due to obtaining of combinatorial derivative of dipiridamol, the effective dose of dipiridamol can be reduced by 5 orders of magnitude to completely inhibit DPE.

The following table 2 shows the formulations of the studied pharmaceutical compositions.

TABLE 2

Formulation and ratio of ingredients of the pharmaceutical composition (FC CD) per capsule or pill

| Item No. | Ingredient name | % |
|---|---|---|
| 1 | 2 | 3 |
| 1. | CD | 0.1-20.0 |
| 2. | Papaverine | 0.5-10.0 |
| 3. | Ascorbic acid | 0.2-10.0 |
| 4. | Bendazole | 0.5-10.0 |
| 5. | Tadalafil | 1-5.0 |
| 6. | Sodium valproate | 5-20.0 |
| 7. | Excipients | up to 100% |

As a control, the animals were applied the same composition with the same substances (in the form of Carbopol gel), but without CD (FC).

Example 2. Determination of FC and FCCD Compositions Impact on Tissue Regeneration The wound-healing properties of compositions were studied on male Vistar white rats. 38 animals previously anesthetized had a cut out of the skin area of 2 by 2 cm size on the dorsal side of the body, behind the right shield bone. The skin was taken by forceps and pulled back; the size of skin fragment was 2 cm, cut depth—2 mm, wound average area—4±1.0 $cm^2$. The obtained polygonal shaped wounds bleeded intensively. Then, FC and FCCD were applied to the wound of the group 1 and 2 animals (10 in each). The wounds of group 3 rats were treated with "panthenol", the 4th group of 8 animals was the control group; the wounds of these animals were not treated. The preparations were applied in such a way that the formed gels covered the entire surface of the wound and involved a small fragment around the wound. BF-6 glue was applied on top of the gel and dried; the animals were put back into the cells. 3, 6, 9, 11, and 13 days after the start of experiment (before the wound healing in animals of all groups) a planimetric study was carried out making it possible to judge the features of reparative processes. The wound area was measured as follows: the celluloid film was applied to the wound and wound contours were plotted on the film; after that the wound surface area was determined using graph paper. The results of the first series of experiments (Table 3) showed that under the impact of FCCD composition, wound healing at all study stages was significantly accelerated, while FC accelerated wound healing slightly. The effectiveness of the FCCD composition was statistically higher than that one of FC composition and Panthenol.

TABLE 3

Indicators of cutaneous wound healing in rats under the impact of FCCD and FC compositions.

| Preparation | Composition formulation | n | Wound area* (S) during the monitoring period, cm² (M ± m) | | | | |
|---|---|---|---|---|---|---|---|
| | | | 1-3 day | 3-6 day | 6-9 day | 9-11 day | 11-13 day |
| FCCD | CD, papaverine, ascorbic acid, bendazole, tadalafil, sodium valproate, carbopol and excipients | 10 | 4.1 ± 0.4 | 1.1 ± 0.1 | 0.1 ± 0.1 | — | — |
| FC | papaverine, ascorbic acid, bendazole, tadalafil, sodium valproate, carbopol and excipients | 10 | 4.3 ± 0.4 | 1.7 ± 0.2 | 0.7 ± 0.2 | 0.5 ± 0.1 | — |
| Panthenol | Carbopol | 10 | 4.0 ± 1.1 | 3.5 ± 0.3 | 2.6 ± 0.4 | 1.2 ± 0.3 | 0.3 ± 0.1 |
| Control | — | 8 | 4.0 ± 0.6 | 3.6 ± 0.6 | 2.6 ± 0.6 | 1.5 ± 0.5 | 0.5 ± 0.2 |

* $P \leq 0.05$

As Table 3 shows that in fact, wounds in animals treated with FCCD composition were healed 2 times faster (13 to 6 days), while the efficacy of control sample Panthenol did not differ from the control. Wound epithelization was initiated on the second day after composition application.

Example 3. Rise of Level of Cells-Precursors in Mice (Pluripotent)

TABLE 5

Absolute count of cells-precursors in 1 ml of blood

| | Methylcellulose culture | | |
|---|---|---|---|
| | CFU-GM | BFU-E | CFU-GEMM |
| Control | 188.2 | 17 | 18 |
| FCCD: 10 mg/kg | 831.7 | 122.7 | 80.9 |

TABLE 5-continued

Absolute count of cells-precursors in 1 ml of blood

| FCCD: 5 mg/kg | 611.5 | 93.3 | 71.7 |
|---|---|---|---|
| FCCD: 2.5 mg/kg | 689.7 | 99.9 | 77.2 |
| FCCD: 1 mg/kg | 426 | 62 | 27.7 |

| | Precursors | | |
|---|---|---|---|
| | Methylcellulose culture | | |
| Time | GM | BFU-E | CFU-GEMM |
| 15" | 2.88 | 2.85 | 3.87 |
| 30" | 6.74 | 4.28 | 4.67 |
| 2' | 2.90 | 2.16 | 1.93 |

(pluripotent)

The impact on subcutaneous (s.c.) administration of FCCD to C3H/H3 J mice for a number of granulocyte macrophage (CFU-GM), erythroid (BFU-E), and polypotent (KOEGEMM) cells-precursors in 1 ml of blood was evaluated. For in vitro colony formation, the precursors were stimulated with a combination of 1 U/ml rhu Epo, 50 ng/ml SLE, conditioned spleen murine cell medium containing 5% v/v. pituitary mitogen (PWMSCM), and 0.1 mM of hemin Plates were counted after 7 days of incubation.

The number of precursor cells of mobilized FCCD was observed versus the time with 5 mg/kg single subcutaneous injection and the results are given in Table 4.

TABLE 4

Absolute count of cells-precursors in 1 ml of blood

| | Methylcellulose culture | | |
|---|---|---|---|
| | CFU-GM | BFU-E | CFU-GEMM |
| Control | 290.2 | 48.3 | 26.1 |
| FCCD: 15" | 793.7 | 129.4 | 92.3 |
| FCCD: 33" | 1803.3 | 210.1 | 116.7 |
| FCCD: 120" | 830.6 | 103.2 | 50.3 |

To evaluate the dose-dependent effects, FCCD was administered at a concentration of 1, 2.5, 5 and 10 mg/kg by a single subcutaneous injection and the number of precursors in 1 ml of blood was determined 1 hour after administration, the results are given in Table 5. The maximum mobilization of precursor cells when using a dose of 2.5-10 mg/kg FCCD achieved approximately 0.5-1 hour after injection, as shown in the Table 6.

Mobilization of Mouse Precursors-Cells when Combined with MIP-1α and G-CSF

The ability of FCCD combined with the macrophage mouse inflammation protein (mu) (MIP-1a), to mobilize precursor cells with or without prior administration of rhu G-CSF was studied. It has been previously demonstrated that MIP-1α promotes the mobilization of precursor cells in mice and humans (Broxmeyer, H. E. et al. Blood Cells, Molecules and Diseases (1998) 24 (2): 14-30). Groups of mice were randomized for subcutaneous injection of a control diluent (physiological salt solution) or G-CSF at a dose of 2.5 μg per mouse twice a day for two days. Eleven hours after the last injection of physiological salt solution or G-CSF, the mice were divided into groups that received MIP-1α administered intravenously at a total dose of 5 μg, FCCD administered subcutaneously at a dose of 5 mg/kg, or a combination of MIP-1α and FCCD at the same doses. In an hour, the mice were sacrificed and the number of precursor cells in 1 ml of blood was determined. FCCD acted more efficiently than the additive method in mobilizing precursor cells when used combined with macrophage mouse inflammation protein (mu) (MIP)-1α, each administered 11 hours after administration of rhu G-CSF or control diluent (physiological salt solution) and 1 hour before taking blood.

Clinical Rise of Level of Cells-Precursors

The study was carried out on five healthy volunteers (P1-P5) with an initial number of white blood cells from 4500 to 7500 cells/mm3. Each patient received a single subcutaneous (s.c.) injection of 80 μg/kg FCCD in 0.9% physiological salt solution from stock solution of 10 mg/ml FCCD in saline under sterile conditions. Blood samples were taken using a catheter prior to dosing and at various time periods up to 24 hours after administration of preparation. Blood samples were evaluated relative to the total count of white blood cells, CD34-positive precursor cells (using FACS analysis) as CD34-positive precursor cells (using FACS analysis) as a percentage of the total count of white blood cells, as well as the absolute count in 1 ml and circulatory status of granulocyte-macrophage (CFU-GM), erythroid (BFU-E) and pluripotent (KOEGEMM) precursor cells. As Tables 4 and 5 show, FCCD administration caused rise of the count of white blood cells and CD34-positive precursor cells in volunteers, which turned out to be maximum 6 hours after administration.

TABLE 6

FCCD-induced mobilization of white blood cells in different volunteers (x10$^3$ WBC)

| Test-ID | Initial data | Treatment, hours | | | | | |
|---|---|---|---|---|---|---|---|
| | | 0.5 | 1 | 2 | 4 | 6 | 9 | 12 |
| P1 | 6.9 | 6.5 | 8.15 | 14.9 | 21.9 | 23.9 | 28.7 | 22.53 | 7.15 |
| P2 | 6.12 | 5.7 | 6.77 | 8.97 | 16.7 | 19.0 | 19.9 | 21.6 | 9.12 |
| P3 | 4.52 | 5.5 | 7.63 | 9.44 | 17.9 | 18.15 | 19.9 | 19.94 | 5.12 |
| P4 | 5.17 | 5.29 | 4.25 | 7.73 | 12.7 | 16.13 | 16.8 | 18.5 | 5.16 |
| P5 | 4.55 | 5.16 | 6.18 | 8.64 | 10.9 | 16.83 | 19.32 | 19.14 | 4.93 |

TABLE 7

FCCD-induced mobilization of CD34-positive cells expressed as a percentage of the total count of WBC in different volunteers

| | | Treatment, hours | | | | |
|---|---|---|---|---|---|---|
| ID | Initial data | 1 | 3 | 6 | 9 | 2 |
| P1 | .06 | .03 | .09 | .12 | .12 | .09 |
| P2 | .07 | .08 | .09 | .13 | .12 | .12 |
| P3 | .06 | .16 | .07 | .08 | .13 | .09 |
| P4 | .06 | .09 | .09 | .11 | .10 | .10 |
| P5 | .12 | .12 | .13 | .2 | .2 | .16 |

The blood was also studied for the mentioned FCCD activated precursors.

The absolute count of undivided nuclear cells and low density nuclear cells in 1 ml of blood was determined (separation in Fico-hypaque), as well as the absolute count in 1 ml and the status in the circulation of granulocyte-macrophage (CFU-GM), erythroid (BFU-E) and polypotent (KOGHEMM) precursor cells in normal donors injected subcutaneously with FCCD. The above indicators were evaluated before administration and 1, 3, 6, 9 and 24 hours after FCCD administration. All results for precursor cells are given based on the rating of 3 culture plates per point analysis. The count of precursor cells and status in circulation, count of CFU-GM, BFU-E and KOEGEMM were studied in methyl cellulose cultures with cell stimulation of 1 U/ml of recombinant human (rhu) erythropoietin, 100 U/ml of rhu granulocyte-macrophage colony stimulating factor (GM-CSF), 100 U/ml rhu of Interleukin-3 (IL-3) and 50 ng/ml of rhu steel factor (SLF=stem cell factor (SCF)). CFU-GM was also evaluated in agar cultures after stimulation with 100 U/ml rhu GM-CSF and 50 ng/ml rhu SLE. In both types of studies, colonies were evaluated after 14 hours of incubation in a humidified atmosphere with 5% $CO_2$ and reduced (5%) $O_2$ pressure. The status of precursor cells in circulation was determined using a highly specific cytolytic method according to the activity of [3H]-thymidine as described previously (Broxmeyer, H. E. et al. Exp. Hematol. (1989) 17:455-459. The results were initially presented as mean total change in the absolute count of nuclear cells and precursors for 1, 3, 6, 9 and 24 hours compared with their count before injection (=Time (T) 0) for all five donors as given below in Tables 8-10: STD—Standard Deviation; STE—Standard Error; PBL-US—peripheral blood-undivided; PBL-LD—peripheral blood—low density (separation in Ficoll); P—Significance using 2-parametric t-test.

TABLE 8

Total change compared to period of time = 0 (Average value from 5 clones)

Content of nuclear cells

| | PBL-US | | | | | PBL-LD | | | | |
|---|---|---|---|---|---|---|---|---|---|---|
| | Average | STD | STE | % CHG | P | Average | STD | STE | % CHG | P |
| T = 0 | 1.00 | 0.00 | 0.00 | 0.0 | 1.00 | 0.00 | 0.00 | 0.0 | | |
| T = 1 | 1.69 | 0.00 | 0.00 | 68.6 | 0.017 | 1.86 | 0.00 | 0.00 | 86.2 | 0.000 |
| T = 3 | 2.80 | 0.51 | 0.23 | 180.2 | 0.000 | 2.86 | 0.28 | 0.12 | 185.6 | 0.000 |
| T = 6 | 3.26 | 0.61 | 0.27 | 225.8 | 0.000 | 3.66 | 0.43 | 0.19 | 266.3 | 0.001 |
| T = 9 | 3.09 | 0.69 | 0.31 | 209.4 | 0.000 | 3.64 | 1.18 | 0.53 | 264.3 | 0.001 |
| T = 24 | 1.07 | 0.65 | 0.29 | 7.0 | 0.553 | 1.05 | 1.19 | 0.53 | 4.6 | 0.815 |

Methylcellulose culture

| | CFU-GM | | | | | BFU-E | | | | | CFU-GEMM | | | |
|---|---|---|---|---|---|---|---|---|---|---|---|---|---|---|
| | Average | STD | STE | % CHG | P | Average | STD | STE | % CHG | P | Average | STD | STE | % CH |
| T = 0 | 1.00 | 0.00 | 0.00 | 0.0 | 1.00 | | 0.00 | 0.00 | 0.0 | | 1.00 | 0.00 | 0.00 | 0.0 |
| T = 1 | 4.77 | 0.00 | 0.00 | 376.7 | 0.001 | 1.99 | 0.00 | 0.00 | 98.9 | 0.002 | 2.32 | 0.00 | 0.00 | 131.8 |
| T = 3 | 13.52 | 1.55 | 0.72 | 1242.5 | 0.001 | 3.21 | 0.50 | 0.22 | 221.3 | 0.004 | 4.33 | 0.44 | 0.20 | 332.5 |
| T = 6 | 21.77 | 5.58 | 2.58 | 2079.6 | 0.000 | 6.01 | 1.25 | 0.56 | 500.5 | 0.006 | 10.07 | 0.59 | 0.27 | 907.2 |
| T = 9 | 10.41 | 5.11 | 2.29 | 952.3 | 0.000 | 4.34 | 2.99 | 1.34 | 334.4 | 0.000 | 5.25 | 4.54 | 2.03 | 425.4 |
| T = 24 | 1.48 | 3.11 | 1.34 | 55.5 | 0.005 | 1.26 | 1.02 | 0.45 | 26.3 | 0.194 | 1.53 | 3.04 | 1.36 | 53.2 |

In this case, the results are presented as the total change from T=0 levels for each individual donor as shown in Tables 8-10.

TABLE 9

Total change compared to period of time = 0 for each individual patient (P)

Content of nuclear cells

| | PBL-US | | | | | PBL-LD | | | | |
|---|---|---|---|---|---|---|---|---|---|---|
| | P1 | P2 | P3 | P4 | P5 | P1 | P2 | P3 | P4 | P5 |
| T = 0 | 1.00 | 1.00 | 1.00 | 1.00 | 1.00 | 1.00 | 1.00 | 1.00 | 1.00 | 1.00 |
| T = 1 | 2.54 | 1.38 | 1.38 | 1.36 | 1.76 | 2.07 | 1.99 | 1.48 | 1.66 | 2.10 |
| T = 3 | 3.55 | 2.74 | 2.02 | 2.46 | 3.23 | 2.83 | 3.25 | 2.17 | 2.82 | 3.20 |
| T = 6 | 3.97 | 2.94 | 2.74 | 2.60 | 4.04 | 4.07 | 3.90 | 2.27 | 2.78 | 5.30 |
| T = 9 | 3.27 | 3.30 | 2.69 | 2.24 | 3.96 | 3.65 | 4.43 | 2.47 | 2.48 | 5.17 |
| T = 24 | 1.21 | 1.43 | 0.96 | 0.77 | 0.99 | 1.01 | 1.71 | 0.79 | 0.60 | 1.12 |

TABLE 10

Precursors
Methylcellulose culture

| | CFU-GM | | | | | BFU-E | | | | | CFU-GEMM | | | | |
|---|---|---|---|---|---|---|---|---|---|---|---|---|---|---|---|
| | P1 | P2 | P3 | P4 | P5 | P1 | P2 | P3 | P4 | P5 | P1 | P2 | P3 | P4 | P5 |
| T = 0 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| T = 1 | 5.09 | 5.33 | 3.70 | 6.87 | 2.84 | 2.58 | 1.46 | 2.30 | 1.46 | 2.13 | 2.07 | 2.26 | 2.22 | 1.96 | 3.07 |
| T = 3 | 7.12 | 17.02 | 15.07 | 20.72 | 8.40 | 5.13 | 1.98 | 2.61 | 2.60 | 3.75 | 4.25 | 3.47 | 4.34 | 5.14 | 4.43 |
| T = 6 | 14.66 | 23.96 | 20.99 | 28.54 | 20.39 | 9.14 | 3.67 | 4.54 | 3.34 | 9.35 | 7.47 | 9.35 | 6.52 | 9.10 | 17.92 |
| T = 9 | 6.26 | 12.51 | 9.42 | 14.08 | 10.09 | 5.43 | 4.61 | 3.71 | 2.93 | 5.05 | 2.64 | 7.09 | 2.47 | 4.52 | 9.55 |
| T = 24 | 1.10 | 1.91 | 1.43 | 1.51 | 1.83 | 1.06 | 1.88 | 1.14 | 0.79 | 1.44 | 1.12 | 2.62 | 0.69 | 0.98 | 2.25 |

As the above tables show, the use of FCCD composition significantly increases the number of all studied classes of pluripotent cells in the blood of volunteers within 6 hours after the start of composition administration.

Example 4. —Reduction of *P. aeruginosa* Virulence Under FCCD Impact on the Example Depression of Adhesive Properties It is known that the adhesion of microorganisms is the first stage of colonization, the main and determining factor of their virulence and pathogenicity. Using adhesins, microbes recognize receptors on cell membranes, attach to them and colonize various surface structures of the cell wall. The ability of bacteria to adhesion and colonization of surfaces is fixed by natural selection. This function is necessary for bacteria with saprophytic existence. For example, *Legionella* are actively attached to the surface of cyanobacteria, cholera vibrios actively colonize zooplankton using their chitin as a source of nutrition and chitin also stimulates the multiplication of cholera vibrios. The study of the microorganisms adhesion is of particular importance for medical microbiology which has received clinical evidence: it was found that in the absence of adhesins, neither bacteria nor fungi can grow and form colonies, and if there is no colonization, then there is no infection and disease.

Adhesion of bacterial pathogen can be carried out to the components of the extracellular matrix—fibronectin, collagen, laminin, etc. Matrix proteins have RGD sequence with which cell surface integrins interact. Thus, extracellular matrix proteins contribute to the adhesion of bacteria to the host target cells. The adhesion of bacteria to such proteins is specific and each pathogen implements this possibility in its own way. For the manifestation of the pathogenicity of some bacteria, their interaction with matrix proteins is critical.

Most gram-negative bacteria attach to epithelial cells of humans and animals using adhesins which are special organelles. Many pathogenic microorganisms are able to penetrate into the host cells and proliferate actively in them. To penetrate into the cells of the bacteria, adhesive molecules called invasins are used. The most common mechanism involves the activation of signals in the host cell allowing the invasion of bacteria by triggering normal cellular reactions. Considering the presence of substances that can affect the manifestation of adhesion, it is possible to direct their action to prevent the development of infectious process. One of the ways to block the adhesion mechanisms is to use anti-infective preparations in low concentrations that inhibit the process of attaching pathogens in the primary infection zone. For this purpose, it is possible to use specific bacteriophages, as well as use in the development of vaccines.

To determine the adhesive properties of microorganisms, the most convenient model in which human red blood cells are used as macroorganism cells. The increase in cell biomass under the influence of enhancers leads to a change in some biochemical tests. One of them is the adhesive properties of microorganisms (Table. 11)

TABLE 11

Comparative adhesive properties (AI) of *P. aeruginosa* over FCCD

| | Adhesion Index (AI) | | |
|---|---|---|---|
| FCCD, % | Pseudomonas aeruginosa ATCC 27853 | Pseudomonas aeruginosa ATCC 9027 | Pseudomonas aeruginosa 12-76 |
| 0.01 ± 0.005 | 2.6 ± 0.3* | 3.4 ± 0.2* | 3.5 ± 0.3* |
| 0.001 ± 0.0005 | 1.8 ± 0.2* | 1.4 ± 0.2* | 1.7 ± 0.4* |
| Control | 3.2 ± 0.3 | 3.1 ± 0.3 | 3.2 ± 0.3 |

Note:
*the difference in indicators is statistically significant ($p < 0.05$)

As shown in data on determination of adhesion degree as per AI during *P. aeruginosa* cultivation on media with FCCD, which are given in Table 11, adhesion indices differed from control indices. FCCD composition expressed in terms of combinatorial dipyridamole at a concentration of 0.001±0.0005% contributed to a decrease in adhesive activity of *Pseudomonas aeruginosa* strains to (1.4±0.3)-(1.8±0.4). Medium-adhesive strains under the influence of FCCD became low-adhesive. Adhesion index was (1.4-1.7) versus (3.1-3.2) when grown on medium without adding FCCD.

As a result of processing the statistical data from Table 11, it was demonstrated that the differences between the adhesion indices of strains cultured on FCCD media at concentrations from 0.001±0.0005% to 0.01±0.005% and control are statistically significant. This indicates the effectiveness of using FCCD in a concentration from 0.001±0.0005% to 0.1±0.05% to reduce the adhesive activity of microorganisms.

Example 5. Reduction of *P. aeruginosa* Virulence Under the Impact of FCCD on the Example of Recovery of the Bacteria Sensitivity to Antibiotics (Inhibition Zones on Solid Nutrient Medium)

The studies are carried out in vitro by diffusion method on P. Aeruginosa strains indicated in previous experiments. Two rows of plates containing Müller-Hinton agar were prepared in parallel, with a 0.01-0.005% FCCD solution added to the second-row plates. After that, bacteria of the studied strains from a suspension containing $10^8$ μl/ml are inoculated on the surface of the agar. To do this, prepare a bacterial suspension corresponding to a concentration of $10^9$ μl/ml according to the optic turbidity standard of 10 units diluted with physiological salt solution 10 times (up to $10^8$ μl/m1). After the suspension is absorbed into agar, discs with polymyxin, ceftriaxone, levofloxacin, amikacin, imipinem are applied to its surface (cefazolin and amoxicillin were also added with additional passages, but they did not appear sensitive). Inoculations on plates with FCCD-free medium are used as controls, as well as media on which discs are not applied. Inoculations are incubated for 48 hours at 37° C. in one passage, then re-inoculation is carried out under similar conditions for the following passages. A total of 4 passages were carried out with controls. The results are taken into account by the diameter of the bacteria inhibition zones. On FCCD-free medium, there are no inhibition zones (an indicator of antibiotic resistance of bacteria), whereas on a medium containing 0.005-0.01% FCCD, a zone of bacterial growth inhibition from 25 to 40 mm in diameter forms around discs (appearance of sensitivity to antibiotic).

As a result of studies, it was found that in FCCD-free medium there is no zone of bacterial growth inhibition around disks with polymyxin and amikacin. With administration of (0.005-0.01)% FCCD (plate 2) into medium around the disks with polymyxin and amikacin, zone of bacterial growth inhibition appears indicating an increase in the bacteria sensitivity to antibiotics. Growth inhibition zones were not observed for antibiotics Pseudomonas aeruginosa has genetically determined (initial) antibiotic resistance. Thus, FCCD composition is able to statistically significantly inhibit acquired antibiotic resistance in Pseudomonas aeruginosa.

Similar studies were conducted for multi-resistant hospital strains K. pneumonia, A. bauiannii, S. aureus. In all cases, the sensitivity of bacteria to antibiotics was recovered at passage 3-4 and did not differ from similar ATCC strains.

Example 6. Reduction of P. aeruginosa Virulence Under the Impact of FCCD on the Example of Recovery of Bacterial Sensitivity to Antibiotics (Growth Inhibition in a Liquid Nutrient Medium, Determination of Changes in MIC)

The study is carried out on P. aeruginosa strains given in the previous examples by in vitro serial dilution method using FCCD. Evaluate the decrease in resistance of Pseudomonas aeruginosa strains to amikacin and polymyxin. Prepare two rows of plates with Müller-Hinton nutrient medium: the first row contains various concentrations of the studied antibiotic (amikacin and polymyxin)—31, 62, 125, 250, 500 µg/ml of medium (double dilution). At the same time, prepare the same row of plates, but add FCCD additionally into the medium at a concentration of (0.0001-0.001) %. Inoculate 0.05 ml (drop) of each test strain on the plates from a bacterial suspension containing $10^8$ µl/ml according to the optic turbidity standard of 10 units. Müller-Hinton medium without antibiotic and Müller-Hinton medium containing 0.0001% of FCCD without antibiotic are used as controls. Inoculations are incubated at 37° C. for 48 hours. The results are considered by the value of MIC (minimum inhibitory concentration) with the obligatory growth of bacteria on control plates (see table 12). The table shows that when bacteria are exposed to FCCD, the causative agent of pseudomonosis reduces resistance to the studied antibiotics by 10 times.

TABLE 12

Determination of the degree of sensitivity recovery of multiresistant nosocomial pathogens under the action of FCCD composition in different concentrations

| Strains | FCCD, % | Antimicrobial agents (MIC, µg/ml) | | | | |
| --- | --- | --- | --- | --- | --- | --- |
| | | Polymyxin | Amikacin | Ceftriaxone | Levofloxacin | Imipinem |
| P. aeruginosa IMI-2016 | Control (without FCCD) | 250 | >500 | >500 | >500 | >500 |
| | FCCD 0.001 | 31 | 15 | 250 | 125 | 250 |
| | FCCD 0.001 | 125 | 125 | 500 | 250 | 125 |
| A. baumannii IMI-2016 | Control (without FCCD) | >500 | >500 | >500 | >500 | >500 |
| | FCCD 0.001 | 31 | 15 | 250 | 125 | 250 |
| | FCCD 0.001 | 62 | 125 | 125 | 62 | 31 |
| K. pneumoniae IMI-2016 | Control (without FCCD) | >500 | >500 | >500 | >500 | >500 |
| | FCCD 0,001 | 62 | 31 | 125 | 125 | 250 |
| | FCCD 0,001 | 125 | 62 | 250 | 250 | 125 |

As Table 12 shows, sensitivity to antibiotics increased 33 times for amikacin and Pseudomonas aeruginosa and 16 times for polymyxin and Pseudomonas aeruginosa. A similar pattern was observed for acinetobacter and Klebsiella. Although sensitivity to other antibiotics also increased 2-4 times, but their concentration did not decrease to values probable for use in humans. Thus, the use of FCCD composition is promising for recovery of sensitivity to antibiotics in multiresistant strains of microorganisms.

The invention claimed is:

1. A pharmaceutical composition, including histone deacetylase inhibitors, dipyridamole and other phosphodiesterase inhibitors, as well as pharmaceutically acceptable excipients, wherein it also contains unseparated mixture of dipyridamole combinatorial derivatives obtained by means of simultaneous modification by at least two covalent modifying agents selected from succinic anhydride, monochloroacetic acid, malic anhydride, acetic anhydride, propionic anhydride, butane anhydride, acetic-propionic anhydride, acetic-butane anhydride, glutaric anhydride, phthalic anhydride, cis-aconitic anhydride, trans-aconitic anhydride, citric anhydride, isolemic anhydride, acetyl chloride, acetyl fluoride, propionyl chloride, butyroyl chloride, and ethoxyoxalyl monochloride.

2. The pharmaceutical composition according to claim 1, wherein it additionally contains ascorbic acid.

3. The pharmaceutical composition according to claim 1, wherein it additionally contains bendazole.

\* \* \* \* \*